(12) United States Patent
Sallvin

(10) Patent No.: US 7,086,098 B2
(45) Date of Patent: Aug. 8, 2006

(54) MECHANICAL BREATHING AID WITH ADAPTIVE EXPIRATION CONTROL

(75) Inventor: Joachim Sallvin, Stockholm (SE)

(73) Assignee: Maquet Critical Care AB, Solna (SE)

( * ) Notice: Subject to any disclaimer, the term of this patent is extended or adjusted under 35 U.S.C. 154(b) by 815 days.

(21) Appl. No.: 10/091,075

(22) Filed: Mar. 5, 2002

(65) Prior Publication Data
US 2003/0168066 A1 Sep. 11, 2003

(51) Int. Cl.
A47K 3/22 (2006.01)

(52) U.S. Cl. .................. 4/613; 4/612; 4/614; 4/679; 52/34; 52/35; 210/164

(58) Field of Classification Search .................. None
See application file for complete search history.

(56) References Cited
U.S. PATENT DOCUMENTS
4,448,192 A 5/1984 Stawitcke et al.

Primary Examiner—Henry Bennett
Assistant Examiner—Azy Kokabi
(74) Attorney, Agent, or Firm—Schiff Hardin LLP

(57) ABSTRACT

A mechanical breathing aid for providing a regulated supply of a breathing gas has an expiratory pressure regulator for regulating gas pressure within an expiration gas flow path dependent on an input regulatory signal and an expiratory pressure sensor disposed to sense an actual gas pressure within the expiration gas flow path and to provide an output signal indicative thereof. A control unit is operably coupled to the expiratory pressure regulator and to the expiratory pressure sensor for calculating a target pressure as a function of time dependent on a value of compliance calculated from measurements of pressure and flow of provided breathing gas made during an inspiration phase, and for generating the regulatory signal dependent on a magnitude of the difference between the target pressure and the actual pressure.

9 Claims, 1 Drawing Sheet

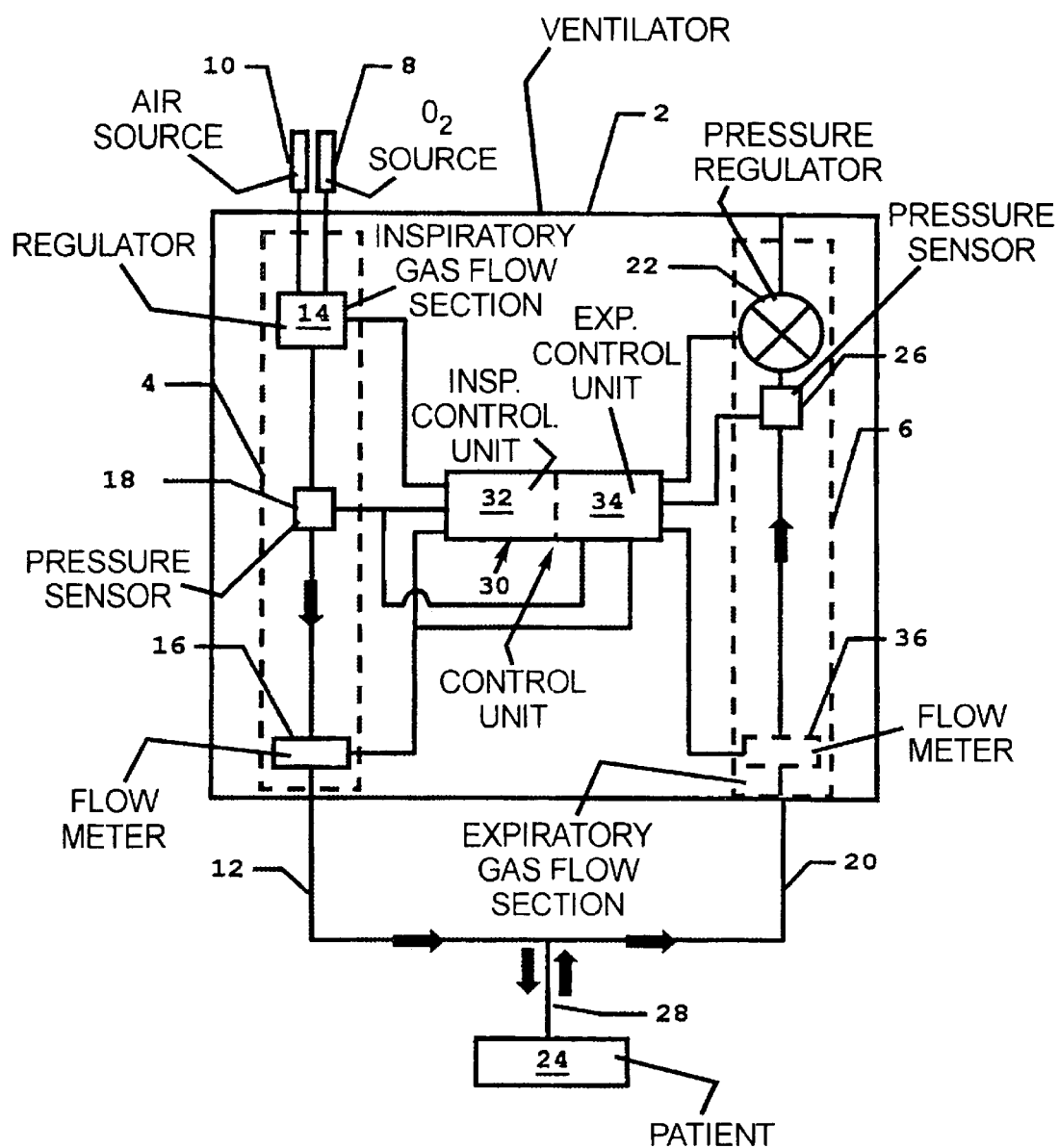

MECHANICAL BREATHING AID WITH ADAPTIVE EXPIRATION CONTROL

BACKGROUND OF THE INVENTION

1. Field of the Invention

The present invention relates to a mechanical breathing aid of the type having an adaptive expiration control.

2. Description of the Prior Art

A breathing aid is known from U.S. Pat. No. 4,448,192 that adapts to a patient's efforts at breathing and to the patient's change in respiratory requirements. An adaptive pressure/volume (P-V) control law is employed for regulating the operation of the breathing aid during one or both of the inspiration phase and the expiration phase of the breathing cycle of the patient. The control law is repeatedly modified for a particular phase dependent on gas parameters measured during the same phase of previous cycles with the goal of enabling the patient to breath with a minimum ventilation opposition, or fighting.

In this known breathing aid the modification of the control law is carried out using estimations of lung compliance and resistance made iteratively over a number of breathing cycles and using fixed adaptation rules. However, the more active the patient the less applicable these rules become, to the extent that in this known breathing aid any measurements made during significant patient activity are ignored in the modification of the control law. Thus a relatively large number of breathing cycles may be required before an optimum adaptation is provided.

SUMMARY OF THE INVENTION

It is an object of the present invention to provide an arrangement for adaptive expiration control in a mechanical breathing aid wherein the adaptation ensues simply and quickly.

This object is achieved in accordance with the principles of the present invention in a mechanical breathing aid for providing a regulated supply of breathing gas, having an inspiratory sensor which measures a tidal volume and pressure of the breathing gas during an inspiration phase, an expiratory pressure regulator which regulates gas pressue within an expiration flow path dependent on a regulatory signal, an expiratory pressure sensor disposed to sense an actual gas pressure within the expiration flow path, and a control unit connected to the expiratory pressure regulator and to the expiratory pressure sensor for calculating a target pressure and for generating the aforementioned regulatory signal dependent on a magnitude of the difference between the target pressure and the actual pressure, and wherein the control means calculates the target pressure as a function of time dependent on a compliance value calculated from the output signals of the inspiratory sensor during an inspiration phase.

The above object also is achieved in a control unit for a mechanical breathing aid which calculates a target pressure as a function of time dependent on a compliance value calculated from pressure and volume measurements of a breathing gas provided by the mechanical breathing aid during an inspiration phase, the control unit generating a regulatory signal dependent on a difference between the target pressure and a measured expiration gas pressure to control an expiratory pressure regulator of the mechanical breathing aid during an expiration phase preferably in a breathing cycle containing the aforementioned inspiration phase.

Thus in the inventive mechanical breathing aid and control unit pressure control during the expiration phase is done as a function of time, dependent on a compliance value calculated from volume and pressure measurements made during an inspiration phase. In this manner the control of the expiration phase is modified by the condition of the respiratory system of a patient connected to the breathing aid. No iterative process is necessary and adaptation can be made essentially immediate.

Preferably these measurements are made during each breathing cycle and employed in the control of the expiration phase of the same cycle. Adaptation is therefore done, and any changes in patient condition accommodated, on a breath-by-breath basis.

The controller may regulate the pressure within the expiratory line so as to allow it to fall below a desired Positive End Expiratory Pressure (so called "PEEP") at the onset of expiration dependent on the condition of the patient lung as estimated, for example, from the compliance. This permits a more rapid removal of inspired gas from the lungs of the patient with a greatly reduced resistance to this from the mechanical breathing aid, thereby reducing the breathing effort and promoting greater breathing comfort.

DESCRIPTION OF THE DRAWING

The single FIGURE is a functional block diagram of a mechanical breathing aid according to the present invention.

DESCRIPTION OF THE PREFERRED EMBODIMENTS

In the FIGURE, the direction of gas flow is illustrated by bold face arrows. A mechanical breathing aid, here represented by a medical ventilator 2, is shown as having an inspiratory gas flow section 4 and an expiratory gas flow section 6. The inspiratory gas flow section 4 is adapted for connection to one or more sources of gas, here illustrated as oxygen 8 and air 10, as well as to an inspiration line 12. The section 4 includes a regulatory arrangement 14 to regulate gas flow from the one or more sources 8, 10 and provide a breathing gas into the inspiration line 12 during an inspiration phase of a patient breathing cycle. An inspiratory flow meter 16 and an inspiratory pressure sensor 18 are provided in the inspiratory section 4 to measure, respectively, the flow and pressure of breathing gas passing into the inspiration line 12.

The expiratory gas flow section 6 is adapted to connect to an expiration line 20 and includes an expiratory pressure regulator 22, such as a solenoid valve, that, by controlling the flow of expiration gas from the airways of a patient 24, regulates the gas pressure within the airways 24 during an expiration phase of a patient breathing cycle. An expiratory pressure sensor 26 is provided to measure expiration gas pressure and is, in this embodiment, located within the expiratory gas flow section 6 of the ventilator 2, proximal the pressure regulator 22.

A conduit 28, such as an endotracheal tube, is arranged to provide a common gas flow path for breathing gas passing from the inspiration line 12 to the airways 24 and expiration gas passing into the expiration line 20 from the airways 24.

A microprocessor control unit 30 is also included within the ventilator 2 and is here programmed to operate both as an inspiratory control unit 32 and as an expiratory control means 34. The inspiratory control unit 32 generates and transmits control signals to the regulatory arrangement 14.

The control signals are typically generated dependent on gas parameters measured by one or both of the flow meter 16 and the inspiratory pressure sensor 18 and on a desired mode of delivery. The choice of delivery mode and the parameters of which will be measured are typically selected by an operator of the ventilator 2 but which may be selected automatically, for example based on a monitored respiratory action of the patient. This regulatory arrangement 14 then operates in response to these control signals to regulate the supply of the breathing gas into the inspiration line 12. The expiratory control means 34 generates and transmits control signals to the expiratory pressure regulator 22. These control signals are, during an expiration phase, generated in response to pressure signals from the expiratory pressure sensor 26 to achieve a desired PEEP pressure.

The manner in which the expiratory control means 34 operates to generate the control signals will be described in more detail below:

The expiratory control means 34 is programmed to operate as a feedback type controller in that the control signals are generated from a comparison between an actual pressure, as measured by the pressure sensor 26, and a target pressure, generated by the control means 34 according to a control algorithm.

By means of the control algorithm the expiratory pressure regulator 22 is operated to permit as high a flow of expiration gas as possible for as long as possible with minimum ventilator resistance, taking into account the requirement to achieve a desired PEEP level, $PEEP_{Set}$, and also the condition of the patient. In order to regulate the lung pressure (as indicated from measurements by the pressure sensor 26) to $PEEP_{Set}$ as quickly as possible it is preferable that the control algorithm is designed to permit the measured pressure to fall below $PEEP_{Set}$ at the beginning of an expiration phase for patients determined to be at little risk if this occurs. It should be noted that the pressure measured by the expiratory pressure sensor 26 located in the expiratory gas flow section 6 will be less than that within the lung while there exists an expiration gas flow. Thus, even though the measured pressure may be allowed to fall below $PEEP_{Set}$ it must not be allowed to fall so much that pressure within the lungs falls to a level below $PEEP_{Set}$.

Regardless of whether the initial pressure is permitted to fall below $PEEP_{Set}$, the control algorithm is adapted to generate the target pressure, PT, as a function of time, t, dependent on a value of compliance, C, calculated from gas parameters measured during an inspiration phase. Thus the control algorithm is designed to adapt to a particular patient and to changes in lung compliance during the provision of mechanical ventilatory assistance.

The tubing of the inspiratory line 12, the gas flow conduit 28 and the airways (primarily the lungs) of a patient 24 may be considered to be a single compliance, C, with no resistance, R, during an inspiration phase. During an inspiration phase the expiratory pressure regulator 22 is operated so that the entire flow, f(t) of breathing gas from the regulatory arrangement 14 passes through the compliance, C. The pressure p(t) as will be measured by the inspiratory pressure sensor 18 may be considered to vary with flow as:

$$p(t) = \frac{1}{C}\int_0^{t1} f(t)dt \qquad (1)$$

where 0 is the start time of an inspiration phase and t1 the end time.

The tidal volume, $V_T$, of breathing gas delivered in the inspiration phase may then be expressed as:

$$V_T \int_0^{t1} f(t)dt \qquad (2)$$

The tidal volume $V_T$ may be readily calculated by integrating, in a known manner, the output from the flow meter 16 throughout the inspiration phase.

Thus the compliance, C, can be expressed as:

$$C = \frac{V_{(Ti)}}{\Delta P} \qquad (3)$$

$\Delta P$ is the pressure difference between end and start pressure during the inspiration phase. The expiratory control unit 34 is for example (as illustrated in FIG. 1) receives the corresponding pressure measurements from the inspiratory pressure sensor 18 and calculates the pressure difference, P. Alternatively the inspiratory control unit 32, the inspiratory pressure sensor 18 or a separate unit may perform this calculation and supply the result to the expiratory control unit 34.

$V_{Ti}$ is the inspired tidal volume which, in the absence of leaks, will be the tidal volume calculated from (2) above.

The inspired tidal volume, $V_{Ti}$ may be calculated within the microprocessor 28 according to:

$$V_{Ti}=V_T-(V_{TOld}-V_{TeOld}) \qquad (4)$$

$V_{TeOld}$ is an inspiration tidal volume of a previous, preferably the immediately preceding, breathing cycle calculated according to equation (1) above.

$V_{TeOld}$ is an expiration tidal volume of the associated expiration phase of the previous breathing cycle and is calculated according to equation (1) with t1 representing the end of the expiration phase, 0 the start of the expiration phase and f(t) an expiration gas flow measured using an expiratory flow meter 36 (broken lines) coupled to measure flow in the expiratory gas flow section 6.

The expiratory control unit 34 is programmed with a control algorithm having the general form:

$$PT(t)=A+Be^{-t/\tau} \qquad (5)$$

The terms A and B are constants selected dependent on the condition of the patient. $\tau$ may be considered a time constant and is dependent on the compliance C. In the present embodiment $\tau$ is calculated within the expiratory control means 34 according to:

$$\tau=C*\kappa \qquad (6)$$

where $\kappa$ is a constant which governs how sensitive the algorithm should be to the calculated compliance, C.

The expiratory control means 34 is preferably programmed to perform the calculation of the compliance, C, for every breath so that the control algorithm (5) adapts to changes in patient condition (namely lung compliance) on a breath-by-breath basis. Such adaptation may be performed even in the presence of significant patient activity since this is accommodated in the calculation of the compliance, C.

In the present embodiment two algorithms are provided, each with different A and B terms and the control means 34 is programmed to select the algorithm for use by comparison of the time constant $\tau$ with a reference value.

If the time constant $\tau$ lies above this reference value then the patient is determined to have relatively healthy lungs and the algorithm:

$$PT9t) = PEEP_{Set} - P_{Offset}e^{\frac{-t}{\tau}} \quad (7)$$

is used.

It will be appreciated that when the expiratory pressure regulator 20 is operated in dependence of this algorithm (7) the pressure in the expiration line 18 is allowed to initially (t=0) fall below the level PEEP$_{Set}$ at the beginning of the expiration phase by an amount P$_{Offset}$, in the present embodiment selected so that pressure within the lungs does not intentionally fall below PEEP$_{Set}$.

If the time constant τ lies below the reference value then the patient is determined to have relatively stiff (low compliance) lungs so that allowing the pressure to drop below PEEP$_{set}$ may be harmful. In this case the expiratory control n means 34 is programmed to calculate the target pressure, PT, according to the algorithm:

$$PT(t) = PEEP_{Set} + \frac{1}{8}P_{Start}e^{\frac{-t}{\tau}} \quad (8)$$

where P$_{Start}$ is the pressure measured by the expiratory pressure sensor 26 at the start (t=0) of the expiration phase.

The values of A and B in equation (5) and the form of the time constant, τ, will depend on the breathing aid used but may be readily determined empirically so as to ensure that pressure in the lungs does not intentionally fall below a desired PEEP, at which the lungs remain open, and that a high rate of flow of expiration gas is possible for as long as possible during an expiration phase.

This determination may be achieved, for example, by attaching the breathing aid to a test-lung, monitoring expiratory pressure and adjusting until a desired expiratory pressure curve is established and by possibly augmenting this with subjective tests to assess breathing "comfort".

Although modifications and changes may be suggested by those skilled in the art, it is in the intention of the inventor to embody within the patent warranted hereon all changes and modifications as reasonably and properly come within the scope of his contribution to the art.

I claim as my invention:

1. A mechanical breathing aid comprising:
    an inspiratory sensor for measuring a tidal volume and pressure of a breathing gas delivered during an inspiration phase of a respiratory cycle, said inspiratory sensor generating inspiratory sensor output signals representing said tidal volume and pressure;
    an expiratory pressure regulator for regulating a gas pressure within an expiration gas flow path dependent on a regulatory signal;
    an expiratory pressure sensor disposed to measure an actual gas pressure within said expiration gas flow path, said expiratory pressure sensor generating an expiratory pressure sensor output signal representing said actual gas pressure; and
    a control unit operatively connected to said expiratory pressure regulator and to said expiratory pressure sensor, said control unit calculating a target pressure dependent on a compliance value calculated by said control unit from the inspiratory sensor output signals during said inspiration phase, and generating said regulatory signal in said respiratory cycle dependent on a magnitude of a difference between said target pressure and said actual pressurre.

2. A mechanical breathing aid as claimed in claim 1 wherein said control unit calculates said target pressure as an exponential varying function of time with a time constant dependent on said compliance value.

3. A mechanical breathing aid as claimed in claim 2 wherein said control unit calculates said target pressure according to A+Be$^{-t/\tau}$, wherein A and B are constants, t is time, and τ is said time constant.

4. A mechanical breating aid as claimed in claim 3 wherein said control unit selects constants A and B dependent on said compliance value.

5. A control unit which generates a regulatory signal dependent on a magnitude of a difference between a target pressure and a measured gas pressure to contorl an expiratory pressure regulator of a mechanical breathing aid during an expiration phase of a respiratory cycle, said control unit calculating a target pressure as a function of time dependent on a compliance value calculated from pressure and volume measurements of a breathing gas provided by said mechanical breathing aid during an inspiration phase.

6. A control unit as claimed in claim 5 wherein said control unit calculates said target pressure as an exponential varying function of time with a time constant dependent on said compliance value.

7. A control unit aid as claimed in claim 6 wherein said control unit calculates said target pressure according to A+Be$^{-t/\tau}$, wherein A and B are constants, t is time, and τ is said time constant.

8. A control unit as claimed in claim 7 wherein said control unit selects constants A and B dependent on said compliance value.

9. A control unit as claimed in claim 5 which calculates said compliance value from said pressure and volume measurements of said breathing gas provided by said mechanical breathing aid during said respiratory cycle.

* * * * *